United States Patent
Basnett

(10) Patent No.: US 7,148,707 B2
(45) Date of Patent: Dec. 12, 2006

(54) NON-CORROSIVE CONDUCTIVITY SENSOR UNIT FOR MEASURING CONDUCTIVITY OF A FLUID

(76) Inventor: Robert Joseph Basnett, 2011 Cupolla Mountain, Cedar Park, TX (US) 78613

( * ) Notice: Subject to any disclaimer, the term of this patent is extended or adjusted under 35 U.S.C. 154(b) by 0 days.

(21) Appl. No.: 10/904,504

(22) Filed: Nov. 13, 2004

(65) Prior Publication Data

US 2005/0115835 A1    Jun. 2, 2005

Related U.S. Application Data

(60) Provisional application No. 60/481,653, filed on Nov. 17, 2003.

(51) Int. Cl.
*G01R 27/08* (2006.01)
(52) U.S. Cl. ........................ 324/700; 324/693
(58) Field of Classification Search ................ 324/446, 324/772, 700, 693
See application file for complete search history.

(56) References Cited

U.S. PATENT DOCUMENTS

| | | | |
|---|---|---|---|
| 5,728,289 A * | 3/1998 | Kirchnavy et al. | 205/775 |
| 6,828,808 B1 * | 12/2004 | Srinivasan et al. | 324/693 |
| 2004/0149663 A1 * | 8/2004 | Nakanishi et al. | 210/748 |
| 2005/0081572 A1 * | 4/2005 | Park et al. | 68/12.02 |

* cited by examiner

*Primary Examiner*—Walter Benson

(57) ABSTRACT

A conductivity sensor includes a sensor body having an inner surface and an outer surface. A first and a second electrode formed of a solid conducting material are positioned through the inner surface of sensor body. An epoxy resin is positioned in the inner surface of the sensor body thereby encapsulating a portion of the first and second electrode. The epoxy resin forms an active surface that exposes a first end of the first and a first end of the second electrode for conductivity measurement and forms a connector surface that exposes a second end of the first and a second end of the second electrode for electrically interfacing with a conductivity measurement circuit.

18 Claims, 4 Drawing Sheets

NON-CORROSIVE CONDUCTIVITY SENSOR UNIT FOR MEASURING CONDUCTIVITY OF A FLUID

This application claims priority to U.S. Provisional Patent Application Ser. No. 60/481,653, filed Nov. 17, 2003, and entitled "Non-Corrosive Conductivity Sensor Unit For Measuring Conductivity Of A Fluid", the entire application of which is incorporated herein by reference.

BACKGROUND OF INVENTION

The present invention relates to conductivity sensors and to method for using conductivity sensors for sensing the conductivity of a fluid. Conductivity sensors are used to measure the conductivity of fluids for numerous types of apparatus. For example, conductivity sensors are used to measure the conductivity of fluids that flow through heat exchangers that control the temperature of equipment, such as semiconductor processing equipment. There are currently more than 15,000 heat exchanger systems in production semiconductor processing equipment that use conductivity sensors to measure the conductivity of cooling fluid flowing through heat exchangers.

BRIEF DESCRIPTION OF DRAWINGS

The aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1A:
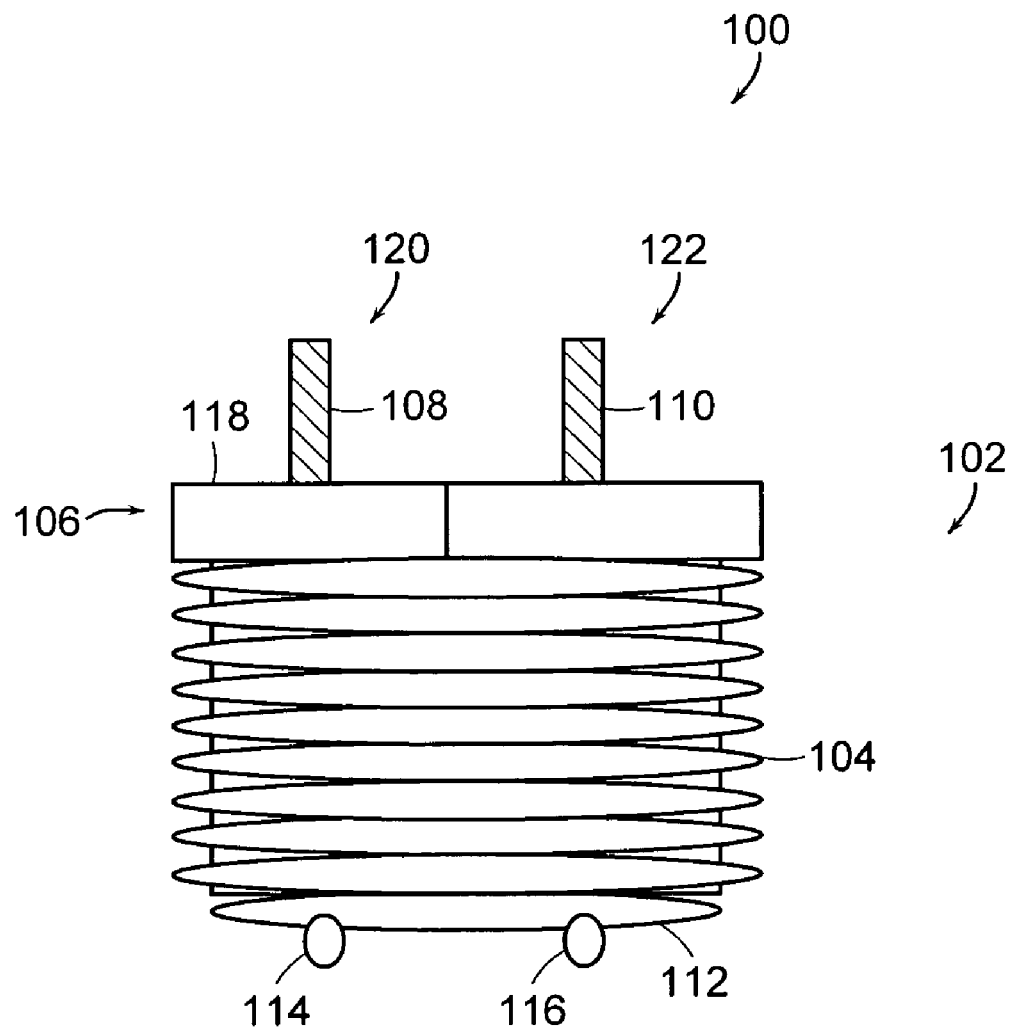
FIG. 1A illustrates a side view of a conductivity sensor according to the present invention.

The conductivity sensor of the present invention is illustrated in connection with measuring the conductivity of a cooling fluid flowing in a heat exchanger that is used to control the temperature of an apparatus used for semiconductor processing. However, the conductivity sensor of the present invention can be used to measure the conductivity of any fluid for any application. The conductivity sensor of the present invention is not limited to applications in semiconductor processing equipment.

Many types of semiconductor processing equipment use fluid cooled heat exchangers to control the temperature of the process chamber and other parts of the equipment. For example, RF plasma processing equipment, such as plasma enhanced chemical vapor deposition (PECVD) systems that are used in the semiconductor industry and other material processing industries, typically include heat exchangers that circulate cooling fluids in order to transfer heat away from the processing chamber and other parts of the equipment.

Many PECVD systems include a gas delivery system having a shower head or a gas box that is coupled to the output of the RF power supply. A portion of the RF energy generated by the RF power supply transfers to the gas delivery system and generates heat energy. Heat exchangers using fluid cooling are typically used to transfer the heat energy away from the gas delivery system and the process chamber with the cooling fluid.

A portion of the RF energy can transfer to the cooling fluid if the conductivity of the cooling fluid is too high. Transferring RF energy into the cooling fluid reduces the power transferred to the plasma and, consequently, lowers the power delivered to the plasma. Lowering the power delivered to the plasma can change the matching conditions between the RF power supply and the plasma and can change other process parameters that could result in process variations. Many PECVD systems carefully monitor the conductivity of the cooling fluid in order to alert a control system or the equipment operator that the conductivity of the cooling fluid is too high and, consequently, a significant amount of RF power may be transferring to the cooling fluid.

Known conductivity measuring systems include a conductivity sensor that has two electrodes that are positioned in an insulating material. The conductivity sensor is designed to be positioned such that the two electrodes are exposed to the cooling fluid. The conductivity of the cooling fluid presents a resistance across the two electrodes. The known conductivity measuring systems also include a circuit that determines the conductivity of the cooling fluid from the resistance presented across the two electrodes.

Known conductivity sensors typically have electrodes that are formed of a base material that is gold plated in order to lower the resistance of the electrodes. Lower resistance electrodes can increase the accuracy of the conductivity measurement. It is desirable to have the resistance of the electrodes be relatively low compared with the resistance of the cooling fluid in order to increase the accuracy of the conductivity measurement. The gold plated electrodes used in known conductivity sensors also protect the base material of the electrodes from corrosion resulting from exposure of the electrodes to the cooling fluid.

Cooling fluids used to transfer heat in heat exchangers have relatively high heat capacity. Commonly used cooling fluids for heat exchangers include, for example, de-ionized water and mixtures of de-ionized water and ethylene glycol. Exposing gold plated electrodes to these cooling fluids over time will cause the gold plating material on the electrode to flake off, thereby exposing the underlying base electrode materials to corrosion. The removed plating material generates debris that can be trapped by the conductivity sensor. This debris can accelerate degradation of the underlying base material of the electrodes.

Corrosion of the underlying base material of the electrodes will change the resistance of the electrode itself. The changes in resistance of the electrodes that are caused by corrosion are difficult to accurately compensate because these changes in resistance vary over time in a non-repeatable manner. Consequently, changes in resistance of the electrodes can cause inaccurate conductivity measurements of the cooling fluids.

Corrosion of the underlying base material of the electrodes will also contaminate the cooling fluid. Contaminating the cooling fluid with corroded base material and loose plating material can change the thermal and electrical properties of the cooling fluid. Furthermore, corrosion of the underlying base material of the electrodes can be a source of cooling fluid leaks because cooling fluid can escape from voids created by corrosion and removal of plating material.

In addition, degradation of the resin based insulator can be accelerated by exposure to the corrosion of the underlying base material.

FIG. 1A illustrates a side view of a conductivity sensor 100 according to the present invention. The conductivity sensor 100 includes a sensor body 102 having a threaded section 104 on an outer surface that is designed to be screwed into a heat exchanger or cooling system. The sensor body 102 can be formed of any material that is chemically resistant to the sensing environment. For example, the sensor body 102 can be formed of stainless steel, brass, or epoxy. The sensor body 102 can also be formed of a composite material or a combination of two or more materials.

The sensor body 102 also includes a head 106 that is formed in the shape of a nut that is designed to fit a wrench or other tool that is used to screw the threaded section 104 of the sensor body 102 into the heat exchanger. In other embodiments, the sensor body 102 does not include the threaded section 104 and the sensor body 102 is attached to a heat exchanger by another means such as welding or epoxy.

The conductivity sensor 100 also includes a first 108 and a second electrode 110 that are positioned through the sensor body 102. The first and second electrodes 108, 110 can be formed in any shape. In one embodiment, the first and second electrodes 108, 110 are cylindrical in shape. The first and second electrodes 108, 110 are formed of a solid conducting material that is chemically resistant to the sensing environment. The solid conducting material forming the electrodes 108, 110 does not need to be plated with any barrier or surface material.

In one embodiment, the first and second electrodes 108, 110 are formed of solid gold. The term "solid gold" is defined herein to mean pure gold or pure gold in an alloy that is anywhere between 1 and 24 karat gold where the term "karat" is a unit of fineness for gold that is equal to 1/24 part of pure gold in an alloy. Solid gold is chemically resistant to cooling fluids that are typically used with heat exchangers, such as de-ionized water and mixtures of de-ionized water and ethylene glycol. Experiments have shown that solid 14K electrodes 108, 110 are impervious to mixtures of de-ionized water and ethylene glycol for extended periods of time. In other embodiments, the first and second electrodes 108, 110 are formed of other solid conducting materials, such as stainless steel and brass.

In one embodiment, a portion of the first electrode 108 and a portion of the second electrode 110 are encapsulated into the sensor body 102 with an insulating potting material, such as epoxy resin. The potting material forms an active surface 112 that exposes a first end 114 of the first electrode 108 and a first end 116 the second electrode 110 for conductivity measurement. The potting material also forms a connector surface 118 that exposes a second end 120 of the first electrode 108 and a second end 122 of the second electrode 110 for electrically interfacing with a conductivity measurement circuit.

Figure 1B:
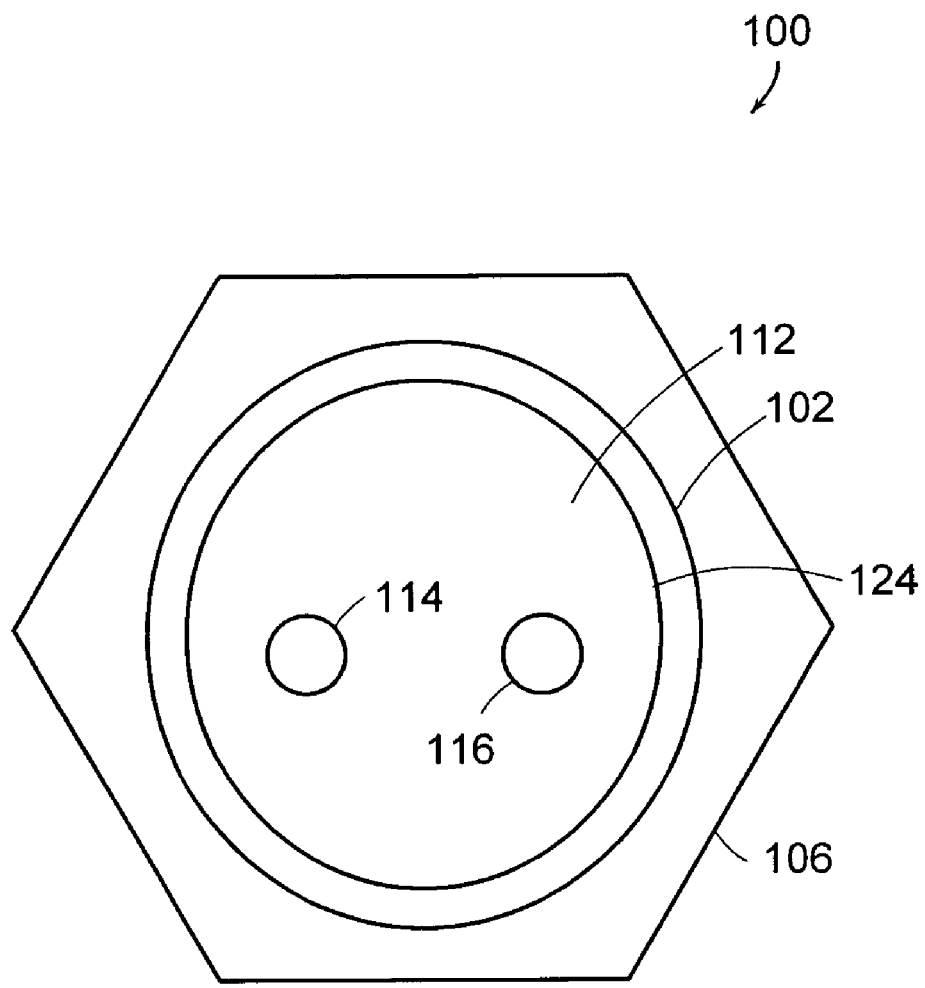
FIG. 1B illustrates a top view of the active surface of the conductivity sensor according to the present invention.

FIG. 1B illustrates a top view of the active surface 112 of the conductivity sensor 100 according to the present invention. The top view shows the first end 114 of the first electrode 108 and the first end 116 the second electrode 110. The top view also shows the sensor body 102 and an inner surface 124 of the sensor body 102 where the potting material bonds to the sensor body 102. Using a suitable potting material eliminates the necessity of using O-ring seals, which tend to degrade over time.

In one embodiment, the potting material is an epoxy resin that is chemically resistant to the cooling fluid and that has a relatively high tensile strength. For example, the potting material can be a two-part epoxy resin that is rated for use above the maximum temperature of the cooling fluid during normal operation of the heat exchanger. An epoxy resin that is rated for use at 300° C. is typically sufficient for most heat exchanger applications. An epoxy resin having a tensile strength that is on the order of 1800 PSI is typically sufficient for most heat exchanger applications. One epoxy that meets the temperature and tensile strength requirements for most heat exchangers applications is J-B Weld epoxy.

The top view also shows the head 106 of the sensor body 102. In the embodiment of the conductivity sensor 100 shown in FIG. 1B, the head 106 is formed in the shape of a hexagon. The hexagon shape of the head 106 is chosen to fit standard wrenches so that the conductivity sensor 100 can be easily screwed into a heat exchanger.

Figure 2:
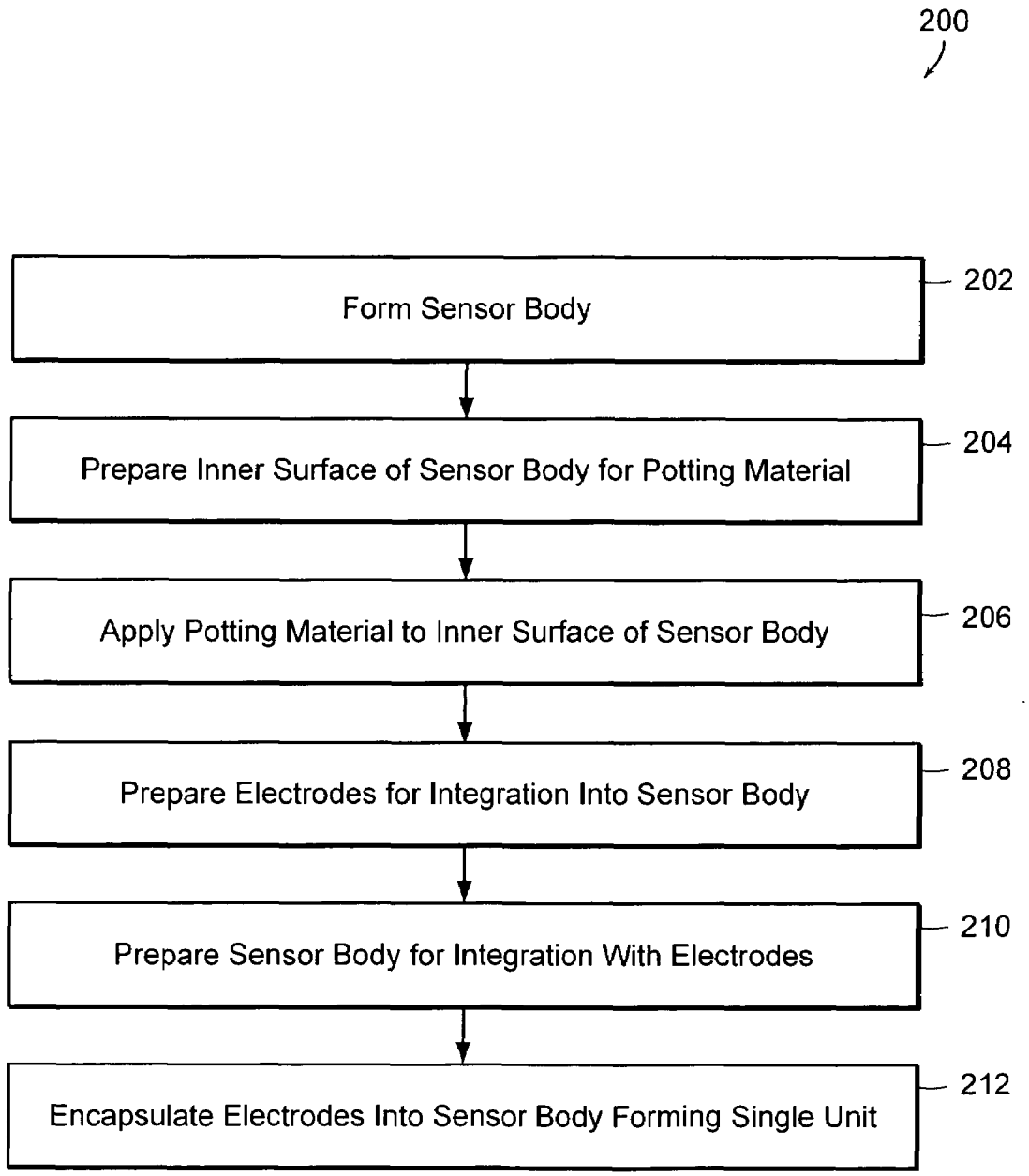
FIG. 2 illustrates a flow chart of a method of manufacturing a conductivity sensor according to the present invention.

FIG. 2 illustrates a flow chart 200 of a method of manufacturing a conductivity sensor according to the present invention. The flow chart 200 is described with reference to the conductivity sensor shown in FIGS. 1A, 1B. In a first step 202, the sensor body 102 is formed. The sensor body 102 can be formed of any material that is chemically resistant to the sensing environment, such as metal, epoxy resin, composite material, or a combination of two or more materials.

In one embodiment, the sensor body 102 is formed of a metal, such as stainless steel or brass. In this embodiment, the sensor body 102 can be a machined part with a threaded section 104, a head 106, and an inner surface 124 as described in connection with FIGS. 1A and 1B. The threaded section 104 can be adapted to be screwed into a heat exchanger or a cooling system. The head 106 can be formed in the shape of a nut that is designed for use with a wrench or other tool. The inner surface 124 can be adapted to form a strong bond with potting material, such as an epoxy resin.

In a second step 204, a surface treatment is performed to promote adhesion of the potting material to the inner surface 124 of the sensor body 102. The surface treatment can include a chemical treatment such as etching and/or a physical erosion treatment, such as sand blasting or bead blasting. Numerous types of surface treatments for promoting adhesion of potting material to the solid conducting materials are known in the art.

In a third step 206, potting material is formed in the inner surface 124 of the sensor body 102. Numerous types of potting material that are known in the art can be used to form an insulator in the inner surface 124 of the sensor body 102. The potting material is then cured to form a solid insulator that is impervious to the sensing environment for an extended period of time, which preferably is the service lifetime of the cooling system and/or the equipment being cooled by the cooling system. In one embodiment, the sensing environment is a cooling fluid, such as a mixture of de-ionized water and ethylene glycol. In this embodiment, the potting material can be an epoxy resin, such as J-B Weld epoxy resin.

In a fourth step 208, the first and second electrodes 108, 110 are prepared for integration into the sensor body 102. The fourth step 208 can include preparing the surface of the first and second electrodes 108, 110 using a chemical treatment such as etching and/or a physical erosion treatment, such as sand blasting or bead blasting. The fourth step 208 can also include soldering contacts for electrical connection. The contacts can be solid gold contacts that are highly resistant to corrosion.

In a fifth step 210, the sensor body 102 is prepared for integrating the first and the second electrodes 108, 110 into the potting material in the inner surface 124 of the sensor body 102. In one embodiment, a first and a second conduit are drilled into the potting material to receive the first and the second electrodes 108, 110. In this embodiment, an alignment jig or template can be used to align a drill bit to the desired location of the first and second electrodes 108, 110.

In a sixth step 212, the first and second electrodes 108, 110 are encapsulated into the senor body 102 to form a single conductivity sensor unit. In this step, the first and second electrodes 108, 110 are positioned in a respective one of the first and second conduits drilled in the fifth step 210 so that the first and second ends 114, 120 of the first electrode 108 and the first and second ends 116, 122 the second electrode 110 are the desired length. The first and second electrodes 108, 110 are then integrated into the potting material. In one embodiment, the first and second electrodes 108, 110 are integrated into the potting material using epoxy resin.

The resulting conductivity sensor manufactured according to the method described in connection with FIG. 2 has no exposed elements that can degrade when in contact with the cooling fluid. Consequently, the conductivity sensor of the present invention has a much longer effective lifetime than known conductivity sensors because it does not corrode significantly when exposed to the sensing environment.

Experiments have shown that a conductivity sensor unit manufactured according to the method described in connection with FIG. 2 had no measurable degradation after 6 months of use. In contrast, the mean lifetime for known conductivity sensors used in heat exchangers for semiconductor processing equipment is approximately three to six months depending on the specific operating environment.

In addition, the entire cooling loop monitored by the conductivity sensor of the present invention has a much longer effective lifetime compared with cooling loops that are monitored by known conductivity sensors because the conductivity sensor of the present invention is not a source of leaks. Furthermore, the entire cooling loop monitored by the conductivity sensor of the present invention has a much longer effective lifetime compared with cooling loops that are monitored by known conductivity sensors because the conductivity sensor of the present invention does not produce debris from plating and insulating materials that degrades the cooling fluid. Consequently, using the conductivity sensor of the present invention will reduce costly maintenance and equipment downtime.

The conductivity sensor of the present invention also provides a more accurate measure of the conductivity of the cooling fluid. A conductivity sensor manufactured using the process described in connection with FIG. 2 presents a resistance that is relatively low compared with the resistance of the cooling fluid. Furthermore, the resistance presented by the conductivity sensor of the present invention is relatively constant over time because corrosion does not increase the resistance of the conductivity sensor.

Figure 3:
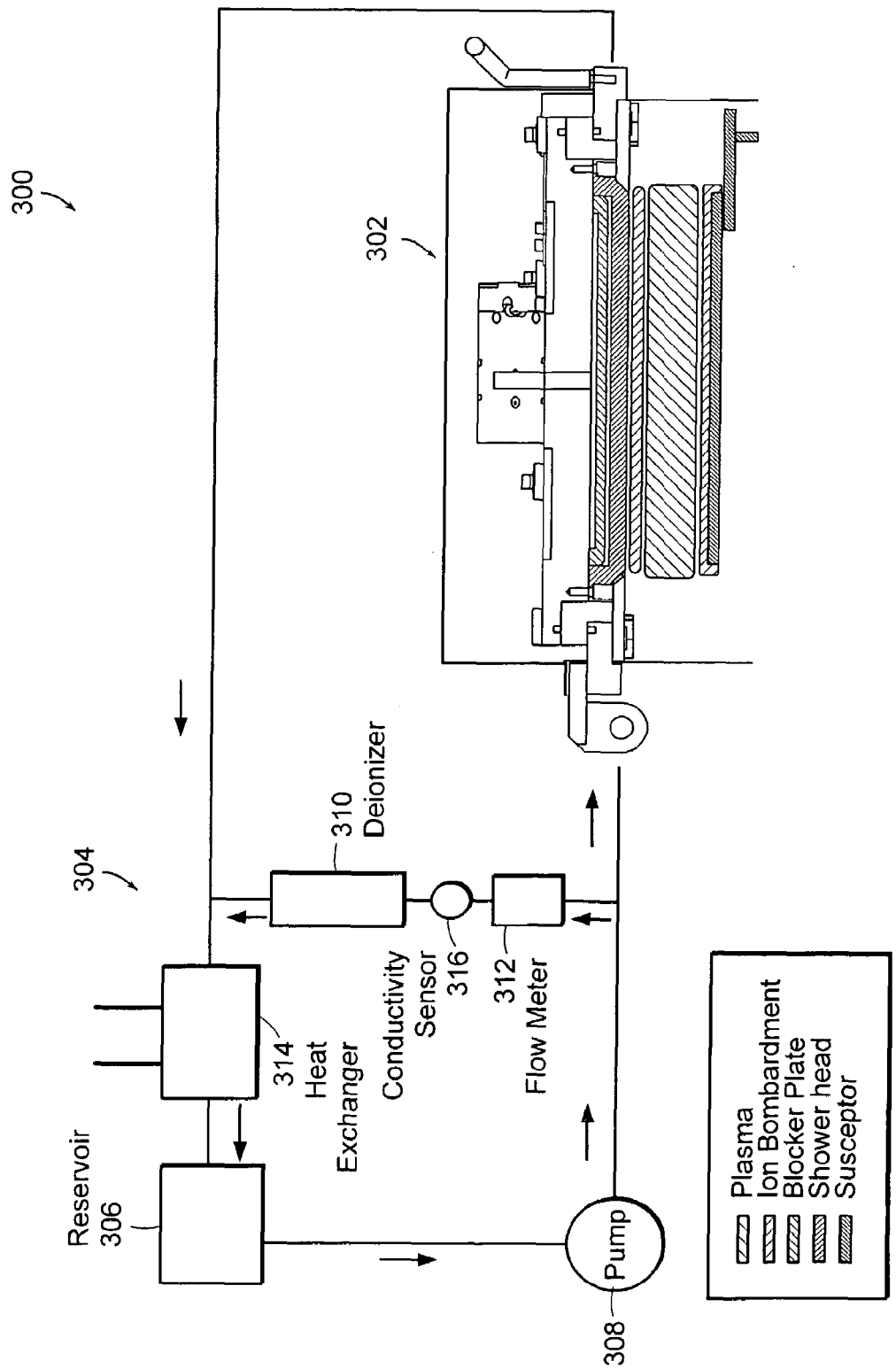
FIG. 3 illustrates a block diagram of a semiconductor processing system having a conductivity sensor according to the present invention.

There are many applications for the conductivity sensor of the present invention. One application is monitoring the conductivity of cooling fluid used to control the temperature of semiconductor processing equipment. FIG. 3 illustrates a block diagram of a semiconductor processing system 300 having a conductivity sensor according to the present invention. The system 300 includes a plasma chamber 302 that generates a plasma for PEVCD and a cooling system 304 for controlling the temperature of the plasma chamber 302. The cooling system 304 can also be used to control the temperature of a remote plasma chamber that is used to clean the plasma chamber or to provide a source of down stream plasma to the plasma chamber 302.

The cooling system 304 includes a cooling fluid reservoir 306 that provides the necessary volume of cooling fluid for cooling the plasma chamber 302. A fluid pump 308 circulates the cooling fluid through the cooling system 304. A deionizer 310 removes ions from the cooling fluid that can cause corrosion. The cooling system 304 can also include a flow meter 312 that monitors the flow rate of the cooling fluid flowing in the cooling system 304.

The cooling system 304 includes a heat exchanger 314 that transfers thermal energy out of the cooling fluid in the cooling system 304. Thermal energy is transferred from the cooling fluid across a barrier in the heat exchanger 314 to a supply of chilled water. A conductivity sensor 316 according to the present invention monitors the conductivity of the cooling fluid flowing in the cooling system.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A conductivity sensor comprising:
   a) a sensor body having an inner surface and an outer surface;
   b) a first electrode that is formed of a solid conducting material comprising at least one of solid 10 carrot gold, solid 14 carrot gold, and solid 18 carrot gold that is positioned through the inner surface of sensor body;
   c) a second electrode that is formed of a solid conducting material comprising at least one of solid 10 carrot gold, solid 14 carrot gold, and solid 18 carrot gold that is positioned through the inner surface of sensor body and adjacent to the first electrode; and
   d) an epoxy resin deposited in the inner surface of the sensor body so as to encapsulate a portion of the first electrode and a portion of the second electrode, the epoxy resin forming an active surface that exposes a first end of the first electrode and a first end the second electrode for conductivity measurement and forming a connector surface that exposes a second end of the first electrode and a second end of the second electrode for electrically interfacing with a conductivity measurement circuit.

2. The sensor of claim 1 wherein the sensor body is formed of stainless steel material.

3. The sensor of claim 1 wherein the sensor body is formed of brass material.

4. The sensor of claim 1 wherein the sensor body is formed of epoxy material.

5. The sensor of claim 1 wherein the outer surface of the sensor body is threaded.

6. The sensor of claim 1 wherein the outer surface of the sensor body comprises a head for securing the sensor body into a manifold.

7. The sensor of claim 1 wherein the epoxy resin comprises a one-part epoxy resin.

8. The sensor of claim 1 wherein the epoxy resin comprises a two-part epoxy resin.

9. The sensor of claim 1 wherein the epoxy resin is chemically resistant to at least one of de-ionized water and ethylene glycol.

10. The sensor of claim 1 wherein the epoxy resin forms a water tight encapsulation of the portion of the first electrode and the portion of the second electrode.

11. The sensor of claim 1 wherein the epoxy resin comprises a tensile strength greater than 1,800 pounds per square inch.

12. A conductivity sensor comprising:
   a) a sensor body that is formed of an epoxy resin;
   b) a first electrode that is formed of a solid conducting material comprising at least one of solid 10 carrot gold, solid 14 carrot gold, and solid 18 carrot gold and that is encapsulated into the epoxy resin of the sensor body; and
   c) a second electrode that is formed of a solid conducting material comprising at least one of solid 10 carrot gold, solid 14 carrot gold, and solid 18 carrot gold and that is encapsulated into the epoxy resin of the sensor body adjacent to the first electrode;
      wherein, the epoxy resin forms an active surface that exposes a first end of the first electrode and a first end of the second electrode for conductivity measurement and forms a connector surface that exposes a second end of the first electrode and a second end the second electrode for electrically interfacing with a conductivity measurement circuit.

13. The sensor of claim 12 wherein an outer surface of the sensor body is threaded.

14. The sensor of claim 12 wherein an outer surface of the sensor body comprises a head for securing the sensor body into a manifold.

15. The sensor of claim 12 wherein the epoxy resin comprises a one-part epoxy resin.

16. The sensor of claim 12 wherein the epoxy resin comprises a two-part epoxy resin.

17. The sensor of claim 12 wherein the epoxy resin is chemically resistant to at least one of de-ionized water and ethylene glycol.

18. The sensor of claim 12 wherein the epoxy resin comprises a tensile strength greater than 1,800 pounds per square inch.

* * * * *